Feb. 2, 1971 H. MATSON Plant Pat. 3,025
APPLE TREE
Filed Feb. 26, 1969
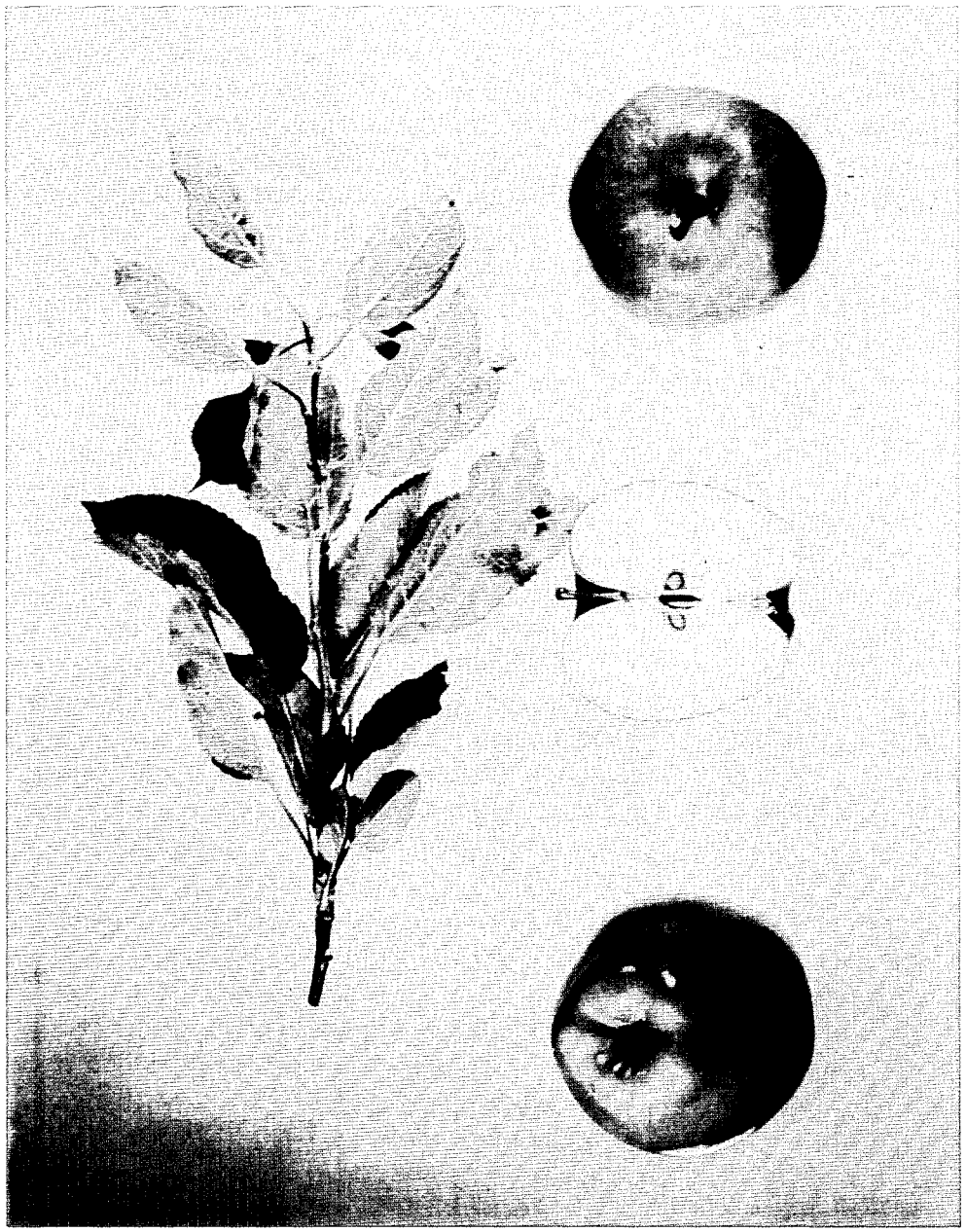
Inventor
Harold Matson
By: Robb & Robb
Attorneys.

United States Patent Office

Plant Pat. 3,025

Patented Feb. 2, 1971

3,025

APPLE TREE

Harold Matson, Zillah, Wash., assignor to Stark Bro's Nurseries & Orchards Company, Louisiana, Mo., a corporation of Missouri

Filed Feb. 26, 1969, Ser. No. 802,692

Int. Cl. A01h *5/03*

U.S. Cl. Plt.—35 1 Claim

The present invention relates to a new and distinct variety of apple tree which was discovered by me as a bud mutation or limb sport of the apple variety commonly known as "Ryan Red Delicious" (unpatented), said discovery having been made by me in my cultivated orchard on property jointly owned by me and another member of my family, and situated at Zillah, in Yakima County, Wash.

At the time of my discovery aforesaid, I was growing in my orchard a block of trees of the "Ryan Red Delicious" variety aforementioned. In the course of one of my pre-harvest inspections of the orchard, my attention was attracted to a particular limb on one tree which bore fruit that was brightly colored much earlier than the fruit on the remainder of the tree as well as on all other trees in the block. Closer inspection and prolonged observation of the limb indicated that it was a sport, and I, thereupon, took steps to preserve the same and keep it under close observation. In due course, I asexually reproduced the mutation by budding, as performed by me in my orchard at Zillah, Wash.

Continued observations of the original sport limb and the progeny derived therefrom by budding as stated above, have convinced me that it is a new and distinct variety, as particularly evidenced by the following unique combination of characteristics which are outstanding therein and which distinguish it from the "Ryan Red Delicious" variety and from all other apple varieties of which I am aware, including all other known strains of "Red Delicious" (unpatented) now in commerce:

(1) A general resemblance of the tree and fruit to the variety "Ryan Red Delicious";

(2) A uniform, more stable bright red fruit blush that is completely free of stripes, as distinguished from the prominently striped color pattern of "Ryan Red Delicious"; and (3) An earlier fruit coloring habit occurring at least a full month before fruit maturity and being earlier than any other known strain of "Red Delicious" now in commerce, with the fruit developing an extra fancy grade color in early August at Zillah, Wash.

The accompanying drawing shows typical specimens of the foliage as borne on a typical branch section, as well as typical specimens of the fruit, and with one of the fruit specimens being shown in cross section, all as depicted in color as nearly true as it is reasonably possible to make the same in a color illustration of this character.

The following is a detailed description of my new variety, with color terminology in accordance with Ridgway's Color Standards and Nomenclature (hereinafter abbreviated as (R)), Munsell Color Chart (hereinafter abbreviated as (M)), and the Horticultural Colour Guide (hereinafter abbreviated as (HCG), as indicated, except where general color terms of ordinary dictionary significance are obvious:

Locality where grown and observed: Zillah, Wash.

Dates of first and last pickings: About Sept. 2 and Sept. 9, respectively.

Tree: Medium large; medium vigorous; spreading; dense; open; rapid-growing; hardy; productive; regular bearing.

*Trunk.*—Medium stockiness; smooth.

*Branches.*—Medium thickness; smooth; little-branching. Color: Dull Purplish Black, Plate L, Color 65" ", Tone M (R). Lenticels: From few to medium number; medium small size.

*Leaves.*—Medium large; medium width; medium length; ovate; taper-pointed; medium thickness; rugose. Length: About 3⅜ inches. Width: about 2⅛ inches. Color: Ivy Green, Plate 0960, p. 187, vol. 2 (HCG), with veins redder than "Ryan" and other strains of "Red Delicious." Margin: Coarsely serrate. Petiole: Medium length; thick.

Flowers:

*Dates of first and full bloom.*—About Apr. 21 and May 1, respectively; medium early as compared with other varieties.

*Size.*—Medium large.

*Color.*—White, with tinge of Deep Pink, Hue 2.5 R 6/11 (M).

Fruit:

*Maturity when described.*—Eating ripe; about mid-September.

*Size.*—Uniform. Axial diameter: about 3½ inches. Transverse diameter: About 3⅛ inches.

*Form.*—Conical; angular.

*Cavity.*—Symmetrical; flaring; arcuate; even; pubescent toward apex. Depth: About ¾ inch. Breadth: About 1¼ inches. Markings: None; red color extends right into basin.

*Basin.*—Symmetrical; rounded; wide; furrowed; pubescent. Depth: About ⅜ inch. Breadth: about 1⅛ inches. Markings: None.

*Stem.*—Stout; pubescent. Length: From about 1 inch to 1½ inches. Breadth: About 1/16 inch. Markings: None.

*Calyx.*—Closed; segments persistent; broadly lanceolate; acute; about ¼ inch long; prostrate; reflexed from base at apex; both outer and inner surfaces pubescent.

*Eye.*—Medium size; open.

*Skin.*—Thick; tough; smooth; glossy; waxed. Dots: Obscure; many; small; depressed; circular; color—strong Yellowish Pink, Hue 5 R 7/9 (M); distribution—over entire surface except calyx basin. Ground color: No undercolor shows when mature, and appears solid red. Color markings: Blushed Strong Red, Hue 5 R 4/12 (M); bright. Bloom: Wanting. Scarfskin: Wanting. General color effect: Solid blushed red which darkens until about a week before harvest maturity and then brightens.

*Flesh.*—Rather juicy. Color: Satiny white tinged with red in cortex near skin vascular bundles and calyx tube. Texture: Firm; fine; crisp. Flavor: Subacid; mild; rich. Aroma: Distinct. Quality: Best.

*Core.*—Distant. Bundle area: Medium size; cordate; symmetrical at base; acute at base. Halves of core area: Equal. Bundles: Inconspicuous; color—reddish tinge. Core lines: Clasping. Carpellary area: Indistinct; small. Calyx tube: Pubescent toward base; funnel form; stem of funnel—long; depth of tube to shoulder—about ⅜ inch; entire depth—about ½ inch. Styles: Present. Stamens: In one distinct whorl; basal. Seed cells: Axile; open; cell walls—thin, tough, length—about 1 3/16 inches, breadth—about ⅝ inch; longitudinal section—obovate; surface—fissured; tufted; cross section—narrow.

Seeds: Usually 11 and all perfect; usually 3 per cell.

*Length.*—About ¼ inch.

*Breadth.*—About 3/16 inch.

*Color.*—Strong Brown, Hue 5 YR 4/5 (M).

Use: Market; dessert.

Keeping quality: Medium; about 120 days in regular refrigerated storage.

Insect and disease resistance: Medium resistance to usual apple insects and diseases, as determined by comparison with other apple varieties grown under the same conditions at Zillah, Wash.

I claim:

1. A new and distinct variety of apple tree, substantially as herein shown and described, characterized particularly as to novelty by the unique combination of a general resemblance of the tree and fruit to the variety "Ryan Red Delicious," a uniform, more stable bright red fruit blush that is completely free of stripes, as distinguished from the prominently striped color pattern of "Ryan Red Delicious," and an earlier fruit coloring habit occurring at least a full month before fruit maturity and being earlier than any other known strain of "Red Delicious" now in commerce, with the fruit developing an extra fancy grade color in early August at Zillah, Wash.

No references cited.

ROBERT E. BAGWILL, Primary Examiner